United States Patent [19]

Rizvi et al.

[11] Patent Number: 4,846,985

[45] Date of Patent: Jul. 11, 1989

[54] ANTIOXIDANT COMPOSITIONS

[75] Inventors: S. Q. Abbas Rizvi, Painesville; Charles P. Bryant, Euclid; Kent B. Grover, Chardon; James N. Vinci, Mayfield Hts. all of Ohio

[73] Assignee: The Lubrizol Corporation, Wickliffe, Ohio

[21] Appl. No.: 838,234

[22] Filed: Mar. 10, 1986

[51] Int. Cl.$^4$ .......................................... C10M 129/10
[52] U.S. Cl. .................... 252/47.5; 252/48.2; 252/51.5 R; 252/391; 252/393
[58] Field of Search ................ 252/47.5, 48.2, 51.5 R, 252/391, 393

[56] References Cited

U.S. PATENT DOCUMENTS

| | | | |
|---|---|---|---|
| 2,691,632 | 10/1954 | Harle | 252/33.6 |
| 3,274,258 | 9/1966 | Odenweller | 260/609 |
| 3,322,649 | 5/1967 | O'Shea | 252/48.2 |
| 3,368,975 | 2/1968 | Davis et al. | 252/51.5 R |
| 3,505,225 | 4/1970 | Wheeler | 252/33.6 |

Primary Examiner—Jacqueline V. Howard
Attorney, Agent, or Firm—James L. Cordek; Robert A. Franks; Joseph P. Fischer

[57] ABSTRACT

A composition is disclosed which comprises:

(A) a compound represented by the formula

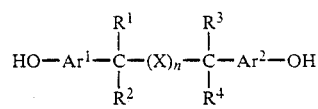

wherein $Ar^1$ and $Ar^2$ are independently mononuclear or polynuclear, substituted or unsubstituted aromatic groups; $R^1$, $R^2$, $R^3$ and $R^4$ are independently hydrogen or hydrocarbyl groups of from 1 to about 25 carbon atoms; X is at least one divalent sulfur atom, sulfone group, sulfixide group, or a mixture thereof; and n is a number ranging from 1 to about 5; and (B) a compound represented by the formula

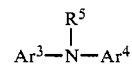

wherein $Ar^3$ and $Ar^4$ are independently mononuclear or polynuclear, substituted or unsubstituted aromatic groups; and $R^5$ is hydrogen, halogen, OH, $NH_2$, SH, $NO_2$ or a hydrocarbyl group of from 1 to about 50 carbon atoms. Concentrates, lubricants, functional fluids, fuels, aqueous compositions and emulsions comprising the foregoing compositions are also disclosed.

24 Claims, No Drawings

ANTIOXIDANT COMPOSITIONS

TECHNICAL FIELD

This invention relates to antioxidants and, more particularly, to antioxidant compositions that are useful in lubricants, functional fluids, normally liquid fuels, emulsions of both the water-in-oil and oil-in-water type, aqueous compositions, and the like.

BACKGROUND OF THE INVENTION

Antioxidants are compounds that are added to organic materials to retard oxidation. Prominant among the general classes of compounds which can be used as antioxidants are sulfides, disulfides, sulfoxides, phosphites, amines, phenols, selenides and zinc dithiophosphates. Examples of such antioxidants include the hindered phenols such as 2,6-di-tertiary-butyl-4-methylphenol, 4,4'-methylene bis(2,6-di-tertiary-butyl phenol) and 4,4'-thiobis (2-methyl-6-tertiary-butyl phenol); and amines such as N-phenyl-alpha-naphthylamine, N-phenyl-beta-naphthylamine, tetramethyldiaminodiphenylmethane, anthranilic acid, phenothiazine and alkylated derivatives of phenothiazine. See, for example, U.S. Pat. Nos. 1,988,299; 2,000,045; 2,202,877; 2,265,582; 2,868,730; 3,032,502; 3,038,858; 3,038,859; 3,043,775; 3,065,178; and 3,132,103; Belgian Patent No. 634,220; and British Patent No. 873,066. Antioxidants are also disclosed in the following publications: "Organic Amines, Hydroxy Compounds Lead Among Anti-Oxidants for Lubricants," Byers, National Petroleum News, Feb. 10, 1937, pp. 67–70; "Lubricating Oil Additives—Oxidation Inhibitors and Detergents," Kalichevsky, Petroleum Refiner 28, No. 9, pp. 85–93, 1949; and "Antioxidants for High Temperature Lubricants," Stemniski et al, Amer. Soc. Lubric. Engineers Preprint No. 63 LC-13, 11 pp., Oct., 1963. These patents and publications are incorporated herein by reference.

While many of the foregoing antioxidants are meritorious, none have provided antioxidant characteristics that are entirely satisfactory. It would be advantageous to provide antioxidants that are more useful in lubricants, functional fluids, normally liquid fuels, emulsions of both the water-in-oil and oil-in-water type, aqueous compositions, and the like.

SUMMARY OF THE INVENTION

The present invention contemplates the provision of antioxidant compositions that are suitable for use in lubricants, functional fluids, normally liquid fuels, emulsions of both the water-in-oil and oil-in-water type, and aqueous compositions, and the like.

Broadly stated, the present invention provides for a composition comprising (A) a compound represented by the formula

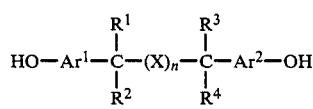

wherein $Ar^1$ $Ar^2$ are independently mononuclear or polynuclear, substituted or unsubstituted aromatic groups; $R^1$, $R^2$, $R^3$ and $R^4$ are independently hydrogen or hydrocarbyl groups of from 1 to about 25 carbon atoms; X is at least one divalent sulfur atom, sulfone group, sulfoxide group, or a mixture thereof; and n is a number ranging from 1 to about 5; and (B) a compound represented by the formula

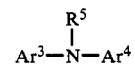

wherein $Ar^3$ and $Ar^4$ are independently mononuclear or polynuclear, substituted or unsubstituted aromatic groups; and $R^5$ is hydrogen, halogen, OH, $NH_2$, SH, $NO_2$ or a hydrocarbyl group of from 1 to about 50 carbon atoms. The invention further provides for concentrates, lubricants, functional fluids, fuels, aqueous compositions, and emulsions containing the foregoing composition.

DESCRIPTION OF THE PREFERRED EMBODIMENTS

The term "hydrocarbyl" is used herein to include substantially hydrocarbyl groups as well as purely hydrocarbyl groups. The description of these groups as being substantially hydrocarbyl means that they contain no non-hydrocarbyl substituents or non-carbon atoms which significantly affect the hydrocarbyl characteristics or properties of such groups relevant to their uses as described herein. Non-limiting examples of substituents which do not significantly alter the hydrocarbyl characteristics or properties of the general nature of the hydrocarbyl groups of this invention include the following:

Ether groups (especially hydrocarbyloxy such as phenoxy, benzyloxy, methoxy, n-butoxy, etc., and particularly alkoxy groups of up to about 10 carbon atoms);

Oxo groups e.g., —O— linkages in the main carbon chain);

Nitro groups;

Thioether groups (especially $C_{1-10}$ alkyl thioether);

Thia groups (e.g., —S— linkages in the main carbon chain);

Carbohydrocarbyloxy groups (e.g.,

hydrocarbyl);

Sulfoxide gripus (e.g.,

hydrocarbyl).
hydrocrbyl).
Sulfone groups (e.g.,

hydrocarbyl);

This list is intended to be merely illustrative and not exhaustive, and the omission of a certain class of substituent is not meant to require its exclusion. The hydrocarbyl groups are preferably free from non-hydrocarbon groups; that is, they are preferably hydrocarbyl groups consisting of only carbon and hydrogen atoms.

The term "lower", as used in the present specification and claims, when used in conjunction with terms such as alkyl, alkenyl, alkoxy, and the like, is intended to describe such groups which contain a total of up to 7 carbon atoms.

The aromatic group, Ar, that is provided for in both components (A) and (B) of the invention can be a mononuclear group such as a phenyl, a pyridyl, a thienyl, a 1,2,3,4-tetrahydronaphthalyl, etc., or it can be a polynuclear group. The polynuclear group can be of the fused type wherein an aromatic nucleus is fused at two points to another nucleus such as found in naphthyl, anthranyl, azanaphthyl, etc. The polynuclear group can also be of the linked type wherein at least two (either mononuclear or polynuclear) are linked to each other. These bridging linkages can be chosen from the group consisting of carbon-to-carbon single bonds, ether linkages, keto linkages, sulfide linkages, polysulfide linkages of 2 to 6 sulfur atoms, sulfinyl linkages, sulfonyl linkages, alkylene linkages, alkylidene linkages, lower alkylene ether linkages, alkylene keto linkages, lower alkylene sulfur linkages, lower alkylene polysulfide linkages of 2 to 6 carbon atoms, amino linkages, polyamino linkages and mixtures of such divalent bridging linkages. In certain instances, more than one bridging linkage can be present in Ar between two aromatic nuclei; for example, a fluorene nucleus having two benzene nuclei linked by both a methylene linkage and a covalent bond. Normally, Ar will contain only carbon atoms in the aromatic nuclei per se although in certain Ar moieties heterocyclic nuclei such as pyridyl, thienyl and furanyl nuclei can be present.

Specific examples of when Ar is a single ring aromatic group include the following:

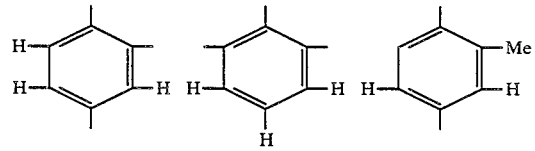

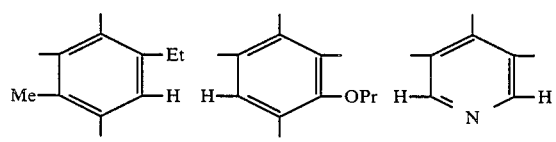

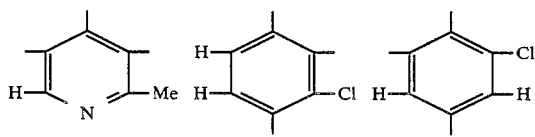

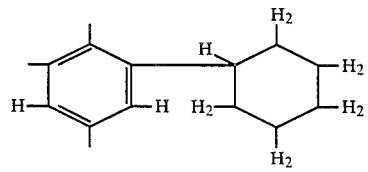

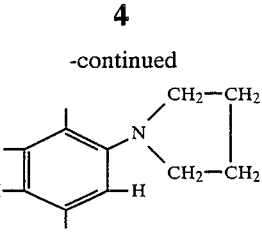

etc. wherein Me is methyl, Et is ethyl and Pr is propyl.

Specific examples of when Ar is a fused ring aromatic group include:

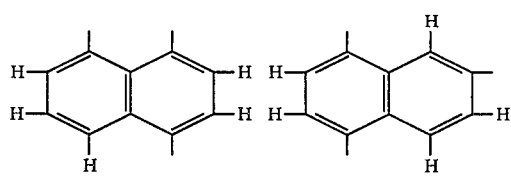

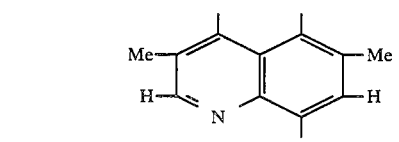

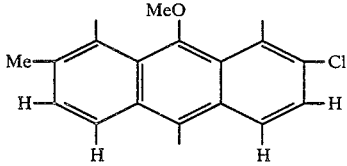

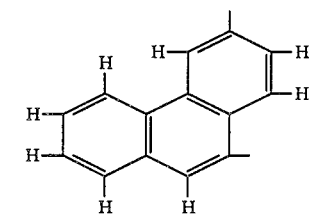

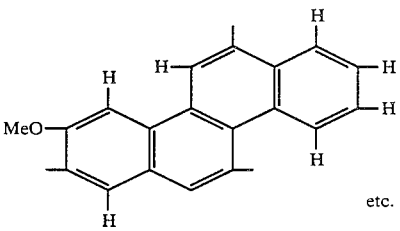

etc.

Specific examples of when Ar is a linked polynuclear aromatic group include:

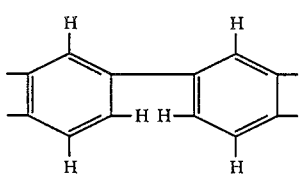

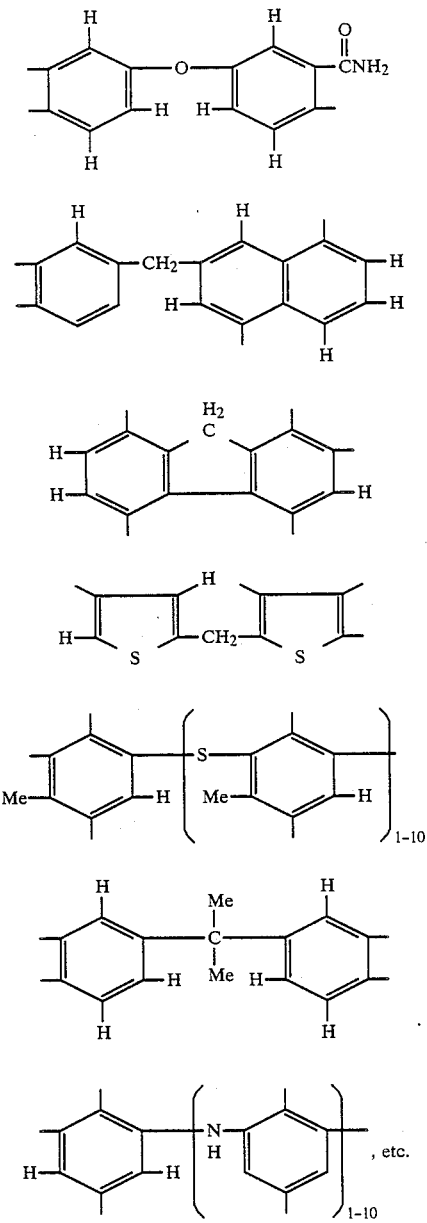

Component A

Component (A) is a compound represented by the formula

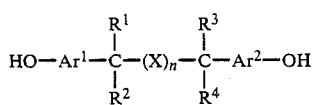

wherein $Ar^1$ and $Ar^2$ are independently mononuclear or polynuclear, substituted or unsubstituted aromatic groups; $R^1$, $R^2$, $R^3$ and $R^4$ are independently hydrogen or hydrocarbyl groups of from 1 to about 25 carbon atoms, more preferably from 1 to about 10 carbon atoms; X is at least one divalent sulfur atom (i.e., —S—), sulfone group (i.e.,

sulfoxide group (i.e., $$-\overset{O}{\underset{}{\overset{\|}{S}}}-),$$

or a mixture thereof; and n is a number ranging from 1 to about 5. Preferably, $Ar^1$ and $Ar^2$ are mononuclear and are the same. X is preferably one or more divalent sulfur atoms. n is preferably a number ranging from 1 to about 3, and more preferably n is 1. When $Ar^1$ and/or $Ar^2$ are substituted aromatic groups, the number of substituents on $Ar^1$ and/or $Ar^2$ ranges independently up to the number of positions available on $Ar^1$ and/or $Ar^2$ for substitution. The substituents on $Ar^1$ and/or $Ar^2$ are preferably selected, independently, from the group consisting of halogen, OH, $NH_2$, SH, $NO_2$ or hydrocarbyl groups of from 1 to about 50 carbon atoms. More preferably, the substituents on $Ar^1$ and $Ar^2$ are hydrocarbyl groups from 1 to about 16 carbon atoms, more preferably from 1 to about 6 carbon atoms.

In a preferred embodiment, component (A) comprises at least one compound represented by the formula

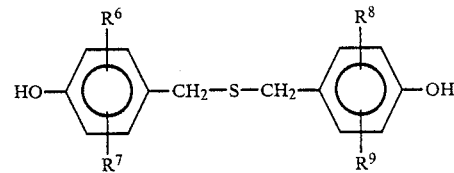

wherein $R^6$, $R^7$, $R^8$ and $R^9$ are independently hydrogen, halogen, OH, $NH_2$, SH, $NO_2$ or hydrocarbyl groups of from 1 to about 50 carbon atoms. Preferably, $R^6$, $R^7$, $R^8$ and $R^9$ are hydrocarbyl groups of from 1 to about 16 carbon atoms, more preferably from 1 to about 6 carbon atoms. In a particularly preferred embodiment, $R^6$, $R^7$, $R^8$ and $R^9$ are each tertiary butyl groups. Component (A) preferably comprises a compound represented by the formula

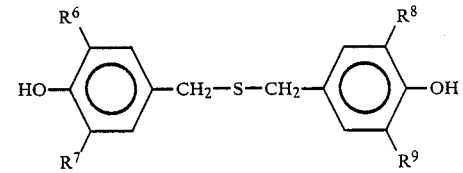

wherein $R^6$, $R^7$, $R^8$ and $R^9$ are as defined above.

In a particularly advantageous embodiment of the invention, component (A) is represented by the formula

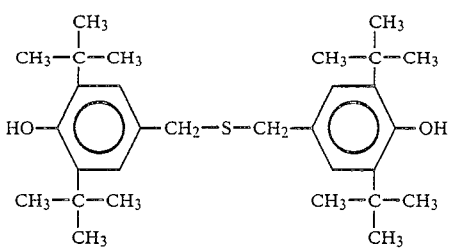

Component (A) can be formed by reacting at least one hydroxyaromatic compound, with at least one aldehyde and/or ketone, and at least one sulfide, in the presence of a suitable solvent. Alternatively, component (A) can be formed by first reacting at least one hydroxyaromatic compound with at least one aldehyde and/or ketone in the presence of a solvent to form an intermediate product; then reacting the intermediate product with at least one sulfide in the presence of a solvent. With either procedure, the molar ratio of aldehyde and/or ketone to hydroxyaromatic compound is preferably from about 1 to about 3 moles of aldehyde and/or ketone per mole of hydroxyaromatic compound. The molar ratio of hydroxyaromatic compound to sulfide is preferably from about 0.5 to about 2 moles of sulfide per mole of hydroxyaromatic compound. The reaction temperature is generally in the range of about 25° C. to about 150° C. and is preferably at the reflux temperature of the reaction mixture.

The hydroxyaromatic compounds are represented by the formulae $Ar^1$-OH and $Ar^2$-OH wherein $Ar^1$ and $Ar^2$ can be the same or different and have the structures described above. Examples of useful hydroxyaromatic compounds include phenol; n-butyl phenol; sec-butyl phenol; tert-butyl phenol; 2-tert-butyl, 4-methyl phenol; 2,4-di-tert-butyl phenol; 2,6-di-tert-butyl phenol; 2-tert-butyl, 4-ethyl phenol; n-amyl phenol; di-tert amyl phenol; hexyl phenols; heptyl phenols; n-octyl phenol; iso-octyl phenol; alpha, alpha, gamma, gamma tetramethylbutyl phenol; nonyl phenol; decyl phenol; tri-isobutyl phenol; and the like. A particularly preferred phenol is 2,6-di-tert-butyl phenol.

The sulfides include monosulfides and polysulfides and are preferably alkali metal sulfides including sodium, potassium, lithium, rubidium and cesium. Monosulfides are preferred. The polysulfides include the mono-, di-, tri-, tetra- and penta-sulfides. The sulfoxyl containing groups (i.e.,

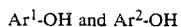

can be prepared from the foregoing sulfides by oxidation according to classical procedures, for example, with hydrogen peroxide in glacial acetic acid. Mixtures of two or more sulfides can be used.

The aldehydes can be any compound of the formulae

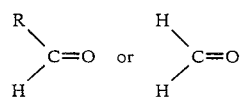

wherein R is a hydrocarbyl group of from 1 to about 25 carbon atoms. Examples of useful aldehydes include formaldehyde, acetaldehyde, propionaldehyde, n-butyraldehyde, n-valeraldehyde, n-caproaldehyde, acrolein, and the like. Formaldehyde is particularly preferred.

The ketones can be any compound of the formula

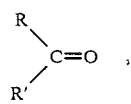

wherein R and R' are independently hydrocarbyl groups of 1 to about 25 carbon atoms. Examples of useful ketones include acetone, methyl ethyl ketone, diethyl ketone, 3-hexanone, t-butyl methyl ketone, cyclopentanone, cyclohexanone, methyl vinyl ketone, mesityl oxide, biacetyl, acetylacetone, and the like.

Preferred solvents include methanol, ethanol, isopropanol and ethylene glycol monoethyl ether. Methanol is particularly preferred since it allows solubility of the reactants and, in many cases, crystallization of the product directly from solution. The reaction is most conveniently carried out at the reflux temperature of the solvent for from about 0.5 to about 24 hours. In those cases where the product does not precipitate on cooling, it can generally be isolated by removal of the solvent or by dilution with water. Liquid products may be isolated in this manner.

The following Examples 1-4 are illustrative of the preparation of component (A) of the invention. Unless otherwise indicated, in the following examples as well as throughout the specification and in the claims, all parts and percentages are by weight and all temperatures are in degrees centigrade.

EXAMPLE 1

2232 grams of Ethyl 733 (a product of Ethyl identified as a mixture of phenols containing at least 75% by weight 2,6-di-tert-butylphenol, and up to 25% by weight of a mixture of 2,4,6-tri-tert-butylphenol and ortho-tert-butylphenol), 4300 grams of methanol and 297 grams of paraformaldehyde are charged to a 12-liter, 4-neck flask. The flask is equipped with a mechanical stirrer, thermowell, nitrogen inlet and a reflux condenser that is vented through a caustic trap. The mixture is stirred under nitrogen and 585 grams of sodium sulfide flakes (60% sodium sulfide) are added in 100-gram portions. When the addition of sodium sulfide is complete, the mixture is heated to reflux. The mixture is maintained at reflux for one hour and then cooled to room temperature. The solid product that separated was collected by filtration, washed thoroughly with tap water and dried.

EXAMPLE 2

1812 grams of Ethyl 733, 4300 grams of methanol and 750 grams of an aqueous solution containing 37% by weight formaldehyde are charged to a 12-liter, 4-neck flask. The flask is equipped with a mechanical stirrer, thermowell, nitrogen inlet and a reflux condenser that is vented through a caustic trap. The mixture is stirred under nitrogen and 595 grams of sodium sulfide flakes (60% sodium sulfide) are added in 100-gram portions. When the addition of sodium sulfide is complete, the mixture is heated to reflux. The mixture is maintained at reflux for one hour and then cooled to room temperature. A solid product is formed. The product is filtered, washed thoroughly with tap water, and then dried in air.

EXAMPLE 3

Part A 1030 grams of 2,6-di-tert-butylphenol, 1600 grams of methanol and 810 grams of an aqueous solution containing 37% by weight formaldehyde are charged to a 5-liter, 4-neck flask. The flask is equipped with a stirrer, thermowell, addition funnel and water-cooled condenser. 31 grams of an 85% by weight aqueous solution of potassium hydroxide are added to the mixture over a period of 20 minutes while maintaining the mixture at 50°–55° C. The mixture is heated to reflux at 75°–80° C. and maintained at reflux for three hours. The mixture is cooled to 60° C. and a solid product is precipitated. The solid product is separated from its mother liquor by decanting off the liquor.

Part B 50 grams of the solid product from Part A, 450 milliliters of methanol and 50 milliliters of tap water are charged to a 1-liter, 3-neck flask equipped with a mechanical stirrer, nitrogen inlet and reflux condenser. 14.3 grams of sodium sulfide flakes (60% sodium sulfide) are added to the mixture under nitrogen, and the mixture is heated to reflux for one hour. The mixture is cooled to room temperature and diluted with water. A solid product is separated from the resulting slurry and dried.

EXAMPLE 4

49.2 grams of Ethanox 754 (a product of Ethyl identified as 4-hydroxymethyl-2,6-di-tert-butylphenol), 450 grams of methanol and 50 grams of water are charged to a 1-liter, 3-neck flask. The flask is equipped with a mechanical stirrer, nitrogen inlet and reflux condenser. The mixture is stirred under nitrogen and 14.3 grams of sodium sulfide flakes (60% sodium sulfide) are added. The mixture is heated to reflux for one hour and then cooled to room temperature. The mixture is then cooled to 0° C. A solid product is separated from the resulting slurry, washed with methanol, and dried in air.

Component (A) can be prepared in accordance with the procedures described in U.S. Pat. Nos. 2,736,703; 3,065,275; 3,252,911; 3,272,869; 3,274,258; 3,322,649; and 3,692,679. These patents are incorporated herein by reference.

Component (B)

Component (B) is a compound represented by the formula

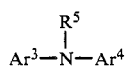

wherein $Ar^3$ and $Ar^4$ are independently mononuclear or polynuclear, substituted or unsubstituted aromatic groups; and $R^5$ is hydrogen, halogen, OH, $NH_2$, SH, $NO_2$ or a hydrocarbyl group of from 1 to about 50 carbon atoms. When $Ar^3$ and/or $Ar^4$ are substituted aromatic groups, the number of substituents on $Ar^3$ and/or $Ar^4$ range independently up to the number of positions available on $Ar^3$ and/or $Ar^4$ for substitution. These substituents are independently selected from the group consisting of halogen (e.g., chlorine, bromine, etc.), OH, $NH_2$, SH, $NO_2$ or hydrocarbyl groups of from 1 to about 50 carbon atoms.

In a preferred embodiment, component (B) is represented by the formula

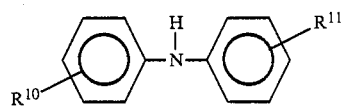

wherein $R^{10}$ and $R^{11}$ are independently hydrogen or hydrocarbyl groups of from 1 to about 50 carbon atoms, preferably hydrocarbyl groups of from about 4 to about 20 carbon atoms. In a particularly advantageous embodiment, component (B) comprises an alkylated diphenylamine such as nonylateddiphenylamine.

U.S. Pat. Nos. 2,558,285; 3,601,632; 3,368,975; and 3,505,225 disclose diarylamines within the scope of component (B). These patents are incorporated herein by reference.

Components (A) and (B) are combined in weight ratios preferably from about 0.01 to about 100 parts of (B) per part of (A), more preferably from about 0.1 to about 50 parts of (B) per part of (A), more preferably from about 0.1 to about 20 parts of (B) per part of (A). A particularly preferred weight ratio for oil-based lubricants is from about 0.1 to about 2 parts of (B) per part of (A). A particularly preferred weight ratio for oil-based hydraulic fluids is from about 2 to about 12 parts of (B) per part of (A).

Lubricants and Functional Fluids

As previously indicated, the compositions of this invention are useful as additives for lubricants and functional fluids, in which they function primarily as antioxidants. These compositions can be employed in a wide variety of lubricants and functional fluids based on a wide variety of oils of lubricating viscosity, including natural and synthetic lubricating oils and mixtures thereof. These lubricants and functional fluids include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Transmission fluids (including both automatic transmission fluids and manual transmission fluids), transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as solvent-refined or acid-refined mineral lubricating oils of the paraffinic, naphthenic, or mixed paraffin-naphthenic types. Oils of lubricating viscosity derived from coal or shale are also useful base oils. Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, etc.); alkyl benzenes (e.g., dodecylbenzenes, tetradecylbenzenes, dinonylbenzenes, di-(2-ethylhexyl) benzenes, etc.); polyphenyls (e.g., biphenyls, terphenyls, alkylated polyphenyls, etc.); and the like.

Alkylene oxide polymers and interpolymers and derivatives thereof where the terminal hydroxyl groups have been modified by esterification, etherification, etc., constitute another class of known synthetic lubricating oils that can be used. These are exemplified by the oils prepared through polymerization of ethylene oxide or propylene oxide, the alkyl and aryl ethers of these polyoxyalkylene polymers (e.g., methylpolyisopropylene glycol ether having an average molecular weight of about 1000, diphenyl ether of polyethylene glycol having an average molecular weight of about 500–1000, diethyl ether of polypropylene glycol having an average molecular weight of about 1000–1500, etc.) or mono- and polycarboxylic esters thereof, for example, the acetic acid esters, mixed $C_3$–$C_8$ fatty acid esters, or the $C_{13}$ oxo acid diester of tetraethylene glycol.

Another suitable class of synthetic lubricating oils that can be used comprises the esters of dicarboxylic acids (e.g., phthalic acid, succinic acid, alkyl succinic acid, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, pentaerythritol, etc.). Specific examples of these esters include dibutyl adipate, di(2-ethylhexyl)-sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethyl-hexanoic acid, and the like.

Esters useful as synthetic oils also include those made from $C_5$ to $C_{12}$ monocarboxylic acids and polyols and polyol ethers such as neopentyl glycol, trimethylol propane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another class of useful oils. These include tetraethyl-silicate, tetraisopropyl-silicate, tetra-(2-ethylhexyl)-silicate, tetra-(4-methyl-hexyl)-silicate, tetra(p-tert-butylphenyl)silicate, hexyl-(4-methyl-2-pentoxy)-di-siloxane, poly(methyl)-siloxanes, poly-(methylphenyl)-siloxanes, etc. Other useful synthetic oils include liquid esters of phosphorus-containing acid (e.g., tricresyl phosphate, trioctyl phosphate, diethyl ester of decane phosphonic acid, etc.), polymeric tetrahydrofurans, and the like.

Unrefined, refined and rerefined oils (and mixtures of each with each other) of the type disclosed hereinabove can be used in the lubricant and functional fluid compositions of the present invention. Unrefined oils are those obtained directly from a natural or synthetic source without further purification treatment. For example, a shale oil obtained directly from a retorting operation, a petroleum oil obtained directly from distillation or ester oil obtained directly from an esterification process and used without further treatment would be an unrefined oil. Refined oils are similar to the unrefined oils except that they have been further treated in one or more purification steps to improve one or more properties. Many such purification techniques are known to those of skill in the art such as solvent extraction, distillation, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed toward removal of spent additives and oil breakdown products.

Generally, the lubricants and functional fluids of the present invention contain an effective amount of the composition of this invention sufficient to provide said lubricants and functional fluids with improved antioxidant properties. Normally this amount will be in the range of from about 0.002% to about 20% by weight, preferably from about 0.05% to about 5% by weight of the total weight of the lubricant or functional fluid.

The invention also contemplates the use of lubricants and functional fluids containing other additives in addition to the antioxidant compositions of this invention. Such additives include, for example, detergents and dispersants of the ash-producing or ashless type, corrosion-inhibiting agents, auxiliary antioxidants, viscosity improving agents, extreme pressure agents, pour point depressants, color stabilizers, anti-foam agents, etc.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of about 1000) with a phosphorizing agent such as phosphorus trichloride, phosphorus heptasulfide, phosphorus pentasulfide, phosphorus trichloride and sulfur, white phosphorus and a sulfur halide or oxygen, or phosphorothioic chloride. Commonly used salts of such acids are those of sodium, potassium, lithium, calcium, mangnesium, strontium and barium.

The term "basic salt" is used to designate metal salts wherein the metal is present in stoichiometrically larger amounts than the organic acid group. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C. and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearyl alcohol, and cyclohexyl alcohol; and amines such as aniline, phenylenediamine, phenothiazine, phenyl-beta-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Ashless detergents and dispersants are so called despite the fact that, depending on its constitution, the dispersant may upon combustion yield a nonvolatile material such as boric oxide or phosphorus pentoxide; however, it does not ordinarily contain metal and therefore does not yield a metal-containing ash on combustion. Many types are known in the art, and any of them are suitable for use in the lubricants of this invention. The following are illustrative:

(1) Reaction products of carboxylic acids (or derivatives thereof) containing at least about 34 and preferably at least about 54 carbon atoms with nitrogen containing compounds such as amine, organic hydroxy compounds such as phenols and alcohols, and/or basic inorganic materials. Examples of these "carboxylic dispersants" are described in British Patent No. 1,306,529 and in many U.S. Patents including the following:

| | | |
|---|---|---|
| 3,163,603 | 3,351,552 | 3,541,012 |
| 3,184,474 | 3,381,022 | 3,543,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | 4,234,435 |
| 3,346,493 | 3,522,179 | Re 26,433 |

(2) Reaction products of relatively high molecular weight aliphatic or alicyclic halides with amines, preferably oxyalkylene polyamines. These may be characterized as "amine dispersants" and examples thereof are described for example, in the following U.S. Patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. Patents are illustrative:

| | | |
|---|---|---|
| 2,459,112 | 3,442,808 | 3,591,598 |
| 2,962,442 | 3,448,047 | 3,600,372 |
| 2,984,550 | 3,454,497 | 3,634,515 |
| 3,036,003 | 3,459,661 | 3,649,229 |
| 3,166,516 | 3,461,172 | 3,697,574 |
| 3,236,770 | 3,493,520 | 3,725,277 |
| 3,355,270 | 3,539,633 | 3,725,480 |
| 3,368,972 | 3,558,743 | 3,726,882 |
| 3,413,347 | 3,586,629 | 3,980,569 |

(4) Products obtained by post-treating the carboxylic, amine or Mannich dispersants with such reagents as urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. Patents:

| | | | |
|---|---|---|---|
| 3,036,003 | 3,282,955 | 3,493,520 | 3,639,242 |
| 3,087,936 | 3,312,619 | 3,502,677 | 3,649,229 |
| 3,200,107 | 3,366,569 | 3,513,093 | 3,649,659 |
| 3,216,936 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,422 |

(5) Interpolymers of oil-solubilizing monomers such as decyl methacrylate, vinyl decyl ether and high molecular weight olefins with monomers containing polar substituents, e.g., aminoalkyl acrylates or acrylamides and poly-(oxyethylene)-substituted acrylates. These may be characterized as "polymeric dispersants" and examples thereof are disclosed in the following U.S. Patents:

| | |
|---|---|
| 3,329,658 | 3,666,730 |
| 3,449,250 | 3,687,849 |
| 3,519,565 | 3,702,300 |

The above-noted patents are incorporated by reference herein for their disclosures of ashless dispersants.

Extreme pressure (E.P.) agents, corrosion-inhibiting agents and auxiliary antioxidants which may be included in the lubricants and functional fluids of the invention are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate, phosphorus esters including principally dihydrocarbon and trihydrocarbon phosphites such as dibutyl phosphite, diheptyl phosphite, dicyclohexyl phosphite, pentylphenyl phosphite, dipentylphenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutylsubstituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

Many of the above-mentioned extreme pressure agents, corrosion inhibitors and auxiliary antioxidants also serve as antiwear agents. Zinc dialkylphosphorodithioates are a well known example.

Pour point depressants are a particularly useful type of additive often included in the lubricants and functional fluids described herein. The use of such pour point depressants in oil-based compositions to improve low temperature properties of oil-based compositions is well known in the art. See, for example, page 8 of "Lubricant Additives" by C. V. Smalheer and R. Kennedy Smith (Lezius-Hiles Co. publishers, Cleveland, Ohio, 1967), which is incorporated herein by reference.

Examples of useful pour point depressants are polymethacrylates; polyacrylates; polyacrylamides; condensation products of haloparaffin waxes and aromatic compounds; vinyl carboxylate polymers; and terpolymers of dialkylfumarates, vinyl esters of fatty acids and alkyl vinyl ethers. Pour point depressants useful for the purposes of this invention, techniques for their preparation and their uses are described in U.S. Pat. Nos. 2,387,501; 2,015,748; 2,655,479; 1,815,022; 2,191,498; 2,666,746; 2,721,877; 2,721,878; and 3,250,715 which are hereby incorporated by reference.

Anti-foam agents are used to reduce or prevent the formation of stable foam. Typical anti-foam agents include silicones or organic polymers. Additional anti-foam compositions are described in "Foam Control Agents", by Henry T. Kerner (Noyes Data Corporation, 1976), pages 125-162, which are incorporated herein by reference.

Components (A) and (B) of the compositions of this invention can be added directly to the lubricant or functional fluid. Preferably, however, they are diluted with a substantially inert, normally liquid organic diluent such as mineral oil, naphtha, benzene, toluene or xylene, to form an additive concentrate. These concentrates usually contain from about 0.2% to about 90% by weight of the antioxidant compositions of this invention and may contain, in addition, one or more other additives known in the art or described hereinabove. The remainder of the concentrate is the substantially inert normally liquid diluent.

In a particularly advantageous embodiment of the invention a rust- and oxidation-inhibited (R&O) oil, turbine oil and/or compressor oil is provided which comprises: a base oil;

from about 0.01% to about 0.25% by weight of a compound represented by the formula

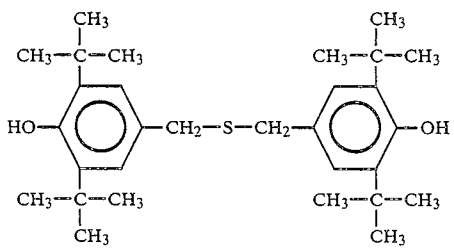

from about 0.01 to about 0.5% by weight of an alkylateddiphenylamine;

from about 0.01 to about 0.1% by weight of a diluent oil;

from about 0.01 to about 0.1% by weight of at least one rust-inhbitor;

from about 0.01 to about 0.1% by weight of at least one metal deactivator;

from about 0.001 to about 0.1% by weight of at least one demulsifier; and from about 0.1 to about 0.5% by weight of at least one auxiliary antioxidant.

In another particularly advantageous embodiment of the invention a hydraulic oil and/or compressor oil is provided which comprises: a base oil;

from about 0.01% to about 0.25% by weight of a compound represented by the formula

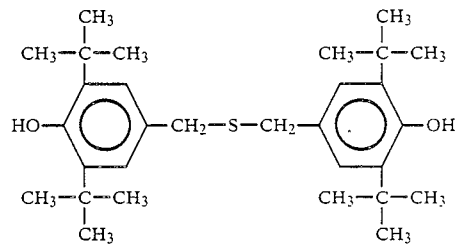

from about 0.01 to about 0.5% by weight of an alkylateddiphenylamine;

from about 0.01 to about 0.1% by weight of a diluent oil;

from about 0.01 to about 0.1% by weight of at least one rust-inhibitor;

from about 0.01 to about 1% by weight of at least one anti-wear agent;

from about 0.01 to about 0.1% by weight of at least one metal deactivator; and from about 0.001 to about 0.1% by weight of at least one demulsifier.

Illustrative lubricants and functional fluids within the scope of the invention are disclosed in Table I. Formulation A is useful as an R&O oil, turbine oil or compressor oil. Formulation B is useful as an anti-wear hydraulic oil or extreme pressure (E.P.) compressor oil. In Table I, all numerical values are in parts by weight.

TABLE I

| | A | B |
|---|---|---|
| Product of Example 1 | 0.01-0.25 | 0.01-0.25 |
| Nonylateddiphenylamine | 0.01-0.5 | 0.01-0.5 |
| Diluent oil | 0.01-0.1 | 0.01-0.1 |
| Commercially available ashless dithiophosphoric acid ester | — | 0.1-1.0 |
| Commercially available propylene tetramer-substituted succinic acid/propylene oxide reaction product | 0.01-0.1 | 0.01-0.1 |
| Tolytriazole | 0.01-0.1 | 0.01-0.1 |
| Tolad 370 (product of Tretolite identified as an ethoxylated glycol) | 0.001-0.1 | 0.001-0.1 |
| Ethyl 732 (product of Ethyl identified as a mixture of 2,6-di-tert-butyl phenol, 2,4,6-tri-tert-butyl phenol and ortho-tert-butyl phenol) | 0.1-0.5 | — |
| Solvent refined high viscosity index base oil | Remainder | Remainder |

Fuels

The fuel compositions of the present invention generally contain a major amount of a normally liquid fuel and a minor amount of the antioxidant composition of the invention. The normally liquid fuel is typically a hydrocarbonaceous petroleum distillate fuel such as motor gasoline as defined by ASTM Specification D439 or a diesel fuel or fuel oil as defined by ASTM Specification D396. Normally liquid fuel compositions comprising non-hydrocarbonaceous materials such as alcohols, ethers, organo-nitro compounds and the like (e.g., methanol, ethanol, diethyl ether, methyl ethyl ether, nitromethane) are also within the scope of this invention as are liquid fuels derived from vegetable or mineral sources such as corn, alfalfa, shale and coal. Normally liquid fuels which are mixtures of one or more hydrocarbonaceous fuels and one or more non-hydrocarbonaceous materials are also contemplated. Examples of such mixtures are combinations of gasoline and ethanol and of diesel fuel and ether. Particularly preferred is gasoline, that is, a mixture of hydrocarbons having an ASTM distillation range from about 60° C. at the 10% distillation point to about 205° C. at the 90% distillation point.

Generally, these fuel compositions contain an antioxidant improving amount of the antioxidant compositions of this invention; usually this amount is from about 1 to about 50,000 parts by weight, preferably from about 4 to about 5000 parts, of the composition of this invention per million parts of fuel.

The fuel compositions can contain, in addition to the composition of this invention, other additives which are well known to those of skill in the art. These include antiknock agents such as tetraalkyl lead compounds, lead scavengers such as haloalkanes (e.g., ethylene dichloride and ethylene dibromide), deposit preventers or modifiers auxiliary such as triaryl phosphates, dyes, cetane improvers, auxiliary antioxidants such as 2,6-di-tertiary-butyl-4-methyl-phenol, rust inhibitors such as alkylated succinic acids and anhydrides, bacteriostatic agents, gum inhibitors, metal deactivators, demulsifiers, upper cylinder lubricants and anti-icing agents.

In certain preferred fuel compositions the compositions of this invention are combined with an ashless dispersant in gasoline. Suitable ashless dispersants include esters of mono- or polyols and high molecular weight mono- or polycarboxylic acid acylating agents containing at least 30 carbon atoms in the acyl moiety. Such esters are well known to those skilled in the art. See, for example, French Patent No. 1,396,645; British Patent Nos. 981,850; 1,055,337 and 1,306,529; and U.S. Pat. Nos. 3,255,108; 3,311,558; 3,331,776; 3,346,354; 3,522,179; 3,579,450; 3,542,680; 3,381,022; 3,639,242; 3,697,428; and 3,708,522. These patents are expressly incorporated herein by reference for their disclosure of suitable esters and methods for their preparation. Generally, the weight ratio of the composition of this invention to the aforesaid ashless dispersant is between about 0.1:1 and about 10:1, preferably between about 1:1 and about 10:1.

Components (A) and (B) of the compositions of this invention can be added directly to the fuel, or they can be diluted with a substantially inert, normally liquid organic diluent such as naphtha, benzene, toluene, xylene or a normally liquid fuel as described above, to form an additive concentrate. These concentrates generally contain from about 0.2% to about 90% by weight of the composition of this invention and may contain, in addition one or more other conventional additives known in the art or described hereinabove.

Emulsions

The emulsions of the present invention can be water-in-oil emulsions or oil-in-water emulsions. Water-in-oil emulsions are characterized by a continuous organic phase and a discontinuous water phase dispersed throughout the organic phase. Oil-in-water emulsions are characterized by a continuous water phase and a discontinuous organic phase dispersed throughout the water phase. Preferably, these emulsions are water-in-oil emulsions. The emulsions of the invention typically comprise from about 1% to about 80% by weight, more preferably from about 30% to about 70% by weight water, and from about 20% to about 99% by weight, more preferably from about 30% to about 70% by weight oil. Any of the natural or synthetic oils identified above can be used in making these emulsions.

Generally, the emulsions of the present invention contain an effective amount of the compositions of this invention to provide said emulsions with improved antioxidant properties. Normally this amount will be from about 0.002% to about 20% by weight, preferably from about 0.05% to about 5% by weight based on the total weight of the emulsion.

These emulsions preferably contain an effective amount of at least one emulsion stabilizer to stabilize the emulsion. Many such emulsion stabilizers are known in the art. Useful emulsion stabilizers include the esters formed by the reaction of at least one substantially saturated hydrocarbyl-substituted succinic acid having at least about 50 aliphatic carbon atoms in the substituent and a polyhydric alcohol. These esters are disclosed in U.S. Pat. No. 3,255,108, which is incorporated herein by reference.

Another class of emulsion stabilizers are the phosphatides, especially those having the structural formula

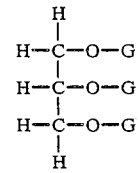

wherein G is selected from the class consisting of fatty acyl groups and phosphorus-containing groups having the structural grouping

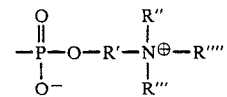

wherein R' is a lower alkylene group having from 1 to about 10 carbon atoms and R", R'" and R"" are lower alkyl groups having from 1 to 4 carbon atoms, and at least one but no more than two of the G groups being said phosphorus-containing group. The fatty acyl groups are for the most part those derived from fatty acids having from about 8 to about 30 carbon atoms in the fatty groups such as octanoic acid, stearic acid, oleic acid, palmitic acid, behenic acid, myristic acid, and oleostearic acid. Especially desirable groups are those derived from commercial fatty compounds such as soyabean oil, cotton seed oil, and castor oil. A particularly effective phosphatide is soybean lecithin which is described in detail in Encyclopedia of Chemical Technology, Kirk and Othmer, Volume 14, pages 250–269 (1981), which is incorporated herein by reference.

The emulsion stabilizer may be an aliphatic glycol or a mono-aryl ether of an aliphatic glycol. The aliphatic glycol may be a polyalkylene glycol. It is preferably one in which the alkylene group is a lower alkylene group having from 1 to about 10 carbon atoms. Thus, the aliphatic glycol is illustrated by ethylene glycol, trimethylene glycol, propylene glycol, tetramethylene glycol, 1,2-butylene glycol, 2,3-butylene glycol, tetramethylene glycol, hexamethylene glycol, or the like. Specific examples of the ethers include monophenyl ether of ethylene glycol, mono-(heptylphenyl) ether of triethylene glycol, mono-(alpha-octyl-betanaphthyl) ether of tetrapropylene glycol, mono-(polyisobutene(- molecular weight of 1000)-substituted phenyl) ether of octapropylene glycol, and mono-(o,p-dibutylphenyl) ether of polybutylene glycol, mono-(heptylphenyl) ether of trimethylene glycol and mono-(3,5dioctylphenyl) ether of tetra-trimethylene glycol, etc. The mono-aryl ethers are obtained by the condensation of a phenolic compound such as an alkylated phenol or naphthol with one or more moles of an epoxide such as ethylene oxide, propylene oxide, trimethylene oxide, or 2,3-hexalene oxide. The condensation is promoted by a basic catalyst such as an alkali or alkaline earth metal hydroxide, alcoholate, or phenate. The temperature at which the condensation is carried out may be varied within wide ranges such as from room temperature to about 250° C. Ordinarily it is preferably 50°–150° C. More than one mole of the epoxide may condense with the phenolic compound so that the product may contain in its molecular structure one or more of the groups derived from the epoxide. A polar-substituted alkylene oxide such as epichlorohydrin or epibromohydrin likewise is useful to prepare the mono-aryl ether product and such product likewise is useful as the emulsion stabilizer in this invention.

Also useful as emulsion stabilizers are the mono-alkyl ethers of the aliphatic glycols in which the alkyl group is, e.g., octyl, nonyl, dodecyl, behenyl, etc. The fatty acid esters of the mono-aryl or monoalkyl ethers of aliphatic glycols also are useful. The fatty acids include, e.g., acetic acid, formic acid, butanoic acid, hexanoic acid, oleic acid, stearic acid, behenic acid, decanoic acid, iso-stearic acid, linoleic acid, as well as commercial acid mixtures such as are obtained by the hydrolysis of tall oils, sperm oils, etc. Specific examples are the oleate of mono-(heptylphenyl)ether of tetraethylene glycol and the acetate of mono-(polypropene(having molecular weight of 1000)substituted phenyl) ether of tri-propylene glycol.

Alkali metal and ammonium salts of sulfonic acids likewise are also useful emulsion stabilizers. The acids are illustrated by decylbenzene sulfonic acid, di-dodecylbenzene sulfonic acid, mahogany sulfonic acid, heptylbenzene sulfonic acid, polyisobutene sulfonic acid (molecular weight of 750), and decylnaphthalene sulfonic acid, and tri-decylbenzene sulfonic acid. The salts are illustrated by the sodium, potassium, or ammonium salts of the above acids.

Also useful as emulsion stablizers are the neutral alkali metal salts of fatty acids having at least 12 aliphatic carbon atoms in the fatty group. These fatty acids include, principally, lauric acid, stearic acid, oleic acid, myristic acid, palmitic acid, linoleic acid, linolenic acid, behenic acid, or a mixture of such acids such as are obtained from the hydrolysis of tall oil, sperm oil, and other commercial fats. The acids should contain at least about 12 aliphatic carbon atoms, preferably from about 16 to about 30 carbon atoms.

Only a small amount of stabilizer is usually required. It may be as little as 0.01 part and seldom exceeds 2 parts per 100 parts of the emulsion. Preferably, it is within the range from about 0.1 to about 1 part per 100 parts of the emulsion.

The emulsions of the invention have a wide variety of uses, particularly as lubricants and hydraulic fluids. These emulsions typically include other additional additives such as extreme pressure agents, rust-inhibiting agents, foam inhibitors, freezing point depressants, bactericides, auxiliary antioxidants, and the like.

Extreme pressure agents that are useful include the lead or nickel or Group II metal phosphorodithioates in which the metal may be magnesium, calcium, barium, strontium, zinc, or cadmium. Zinc is an especially preferred metal. Specific examples of the metal phosphorodithioates include zinc di(4-methyl-2-pentyl) phosphorodithioate, zinc O-methyl-O'-dodecylphosphorodithioate, barium diheptylphosphorodithioate, barium di(n-butylphenyl) phosphorodithioate, magnesium di-cyclohexylphosphorodithioate, cadmium salt of an eqimolar mixture of dimethylphosphorodithioic acid and di-octylphosphorodithioic acid, zinc di-n-nonylphosphorodithioate, zinc di-dodecylphosphorodithioate, lead di-pentyl phosphorodithioate, nickel di-octylphosphorodithioate, and zinc di-(heptylphenyl) phosphorodithioate.

Methods for preparing the phosphorodithioic acids are known in the art, including, for example, the reaction of an alcohol or a phenol with phosphorus pentasulfide. Likewise known are the methods for preparing the Group II metal salts of phosphorodithioic acids. Such methods are illustrated by the neutralization of phosphorodithioic acids or mixtures of such acids with zinc oxide.

Other extreme pressure agents useful in the emulsions of this invention include the chlorinated waxes; sulfurized or phosphosulfurized fatty acid esters; di- and tri-hydrocarbyl phosphites and phosphates; di-hydrocarbyl polysulfides; and metal dithiocarbamates. The chlorinated waxes are exemplified by chlorinated eicosane having a chlorine content of 50% or other chlorinated petroleum waxes having a chlorine content of 5–60%. The sulfurized fatty esters are obtained by the treatment of a lower alkyl ester of a fatty acid aving at least about 12 carbon atoms with a sulfurizing agent such as sulfur, sulfur mono-chloride, sulfur dichloride, or the like. The fatty acid esters are illustrated by methyl oleate, cyclohexyl ester of talc oil acid, etc. Commercial mixtures of esters likewise are useful. They include, for example, sperm oil, Menhaden oil, glycerol trioleate, etc. The sulfurization is effected most conveniently at temperatures between about 100° C. and about 250° C. More than one atom of sulfur can be incorporated into the ester and for the purpose of this invention sulfurized esters having as many as four or five atoms of sulfur per molecule are useful. Examples include sulfurized sperm oil having a sulfur content of 5%, sulfurized tall oil having a sulfur content of 9%, sulfurized methyl oleate having a sulfur content of 3%, and sulfurized oleyl oleate having a sulfur content of 15%.

The phosphosulfurized fatty acid esters are obtained by the treatment of the esters illustrated above with a phosphorus sulfide such as phosphorus pentasulfide, phosphorus sesquisulfide, or phosphorus heptasulfide. The treatment is illustrated by mixing an ester with from about 0.5% to 25% of a phosphorus sulfide at a temperature within the range from about 100° C. to about 250° C. The products contain both phosphorus and sulfur but the precise chemical structure of such products is not clearly understood.

The phosphites and phosphates useful herein are the di- and tri-esters of phosphorus or phosphoric acid in which the ester group is derived from a substantially hydrocarbyl group including aryl, alkyl, alkaryl, arylalkyl, or cycloalkyl group as well as a hydrocarbyl group having a polar substituent such as chloro, nitro, bromo, ether, or the like. Particularly desirable phosphites and phosphates are those in which the ester groups are phenyl, alkylphenyl or alkyl groups containing from about 6 to about 30 carbon atoms. Examples are dibutyl phosphite, diheptyl phosphite, dicylohexyl phosphite, di-(pentylphenyl) phosphite, bis-(dipentylphenyl) phosphite, tridecyl phosphite, di-stearyl phosphite, dimethyl naphthyl phosphite, oleyl 4-pentylphenyl phosphite, triphenyl phosphite, bis-(hexapropylenesubstituted phenyl) phosphite, tri(n-chloro-3-heptylphenyl) phosphite, triphenyl phosphate, tricresyl phosphate, tri(p-chlorophenyl) phosphate, and triheptylphenyl) phosphate.

The metal dithiocarbamates include principally those of zinc, lead, strontium, nickel, cadmium, and palladium and N,N-dialkyldithiocarbamic acids in which the alkyl group contains from 3 to about 30 carbon atoms. Examples are zinc N,N-dioctyl dithiocarbamate, lead N,N-dicyclohexyl dithiocarbamate, cadmium N,N-dibehenyl dithiocarbamate, lead N,N-didodecyl dithiocarbamate, and mixtures thereof.

The concentration of the extreme pressure agent is usually within the range from about 0.05 to about 5 parts, although it is seldom necessary to employ more than 2 parts of this agent per 100 parts of the emulsion.

Another type of additive which finds use in these emulsions is a rust-inhibiting agent. Effective rust-inhibiting agents include the aliphatic amines, especially aliphatic primary amines having at least 8 carbon atoms in the molecule. The aliphatic amines are preferably tertiary-alkyl primary amines having from about 12 to about 30 carbon atoms. The amines include stearyl amine, oleyl amine, myristyl amine, palmityl amine, n-octyl amine, dodecyl amine, octadecyl amine, and other commercial primary amine mixtures such as the mixture in which the aliphatic group is a mixture of tertiary-alkyl group having from 11 to 14 carbon atoms and an average of 12 carbon atoms, and the mixture in which the aliphatic group is a mixture of tertiary-alkyl groups having from 18 to 24 carbon atoms.

Also effective as rust-inhibiting agents are the salts of an aromatic acid such as benzoic acid, toluic acid, naphthoic acid, phthalic acid, or terephthalic acid with any of the aliphatic amines listed above. Salts derived from other acids such as p-aminobenzoic acid and o-chlorobenzoic acid likewise are useful.

The salts of amines with the aromatic acids are prepared simply by mixing the reactants at a temperature below the dehydration temperature, i.e., below about 90° C. In most instances the reaction is exothermic and heating is not necessary. A solvent such as benzene, toluene, naphtha, and chlorobenzene may be used.

Still another class of rust-inhibiting agents are the hydroxy-alkyl amines, especially the long chain (i.e., $C_{8-30}$) aliphatic amines containing one or two hydroxy-alkyl substituents on the amine nitrogen atom. Examples are N-(2-hydroxyethyl) octylamine, N,N-di-(2-hydroxy-1-propyl) dodecylamine, N-(3-hydroxy-1-pentyl) octadecylamine, and N,N-di-(2-hydroxy-3-butyl) decylamine.

Also useful as the rust-inhibiting agents are the nitrous acid salts of the long chain aliphatic amines illustrated above. Such salts are obtained simply by mixing at ordinary temperatures such as room temperature an amine with nitrous acid. Specific examples include the nitrous acid salt of the tertiaryalkyl ($C_{11-14}$) primary amine and the nitrous acid salt of octadecylamine.

The concentration of rust-inhibiting agent in the emulsion depends to some extent upon the relative concentration of water in the emulsion. Ordinarily from about 0.01 part to about 2 parts of a rust-inhibiting agent per 100 parts of the emulsion is sufficient.

Still another type of additive which finds use in these emulsions is a foam-inhibitor which may be a commercial dialkyl siloxane polymer or a polymer of an alkyl methacrylate. Freezing point depressants, i.e., water-soluble polyhydric alcohols such as glycerol or other polar substances such as Cellosolve are also useful. The concentration of these additives usually is less than 5 parts per 100 parts of the emulsion.

Bactericides are also useful in the emulsions of this invention. They are illustrated by nitro-bromoalkanes (such as 3-nitro-1-propyl bromide), nitrohydroxy-alkanes (such as tri-(hydroxymethyl) nitromethane, 2-nitro-2-ethyl-1,3-propan-diol, and 2-nitro-1-butanol), and boric acid esters (such as glycerol borate). The concentration of the bactericide may be from about 0.001 to about 1 part per 100 parts of the emulsion.

Auxiliary antioxidants useful in the emulsions of this invention include the hindered phenols such as 2,4-di-tert-butyl-6-methylphenol, 4,4'-methylene-(2,6-di-tert-butylphenol), and 2,6-di-tert-octyl-4-sec-butylphenol. The concentration of these auxiliary antioxidants is usually from about 0.01 to about 2 parts per 100 parts of the emulsion.

The emulsions can be prepared simply by mixing the oil, water, an emulsion stabilizer, components (A) and (B), and any other ingredient which may be desirable in a homogenizer or any other efficient blending device. Heating the emulsion during or after it is prepared is generally not necessary. The order of mixing of the ingredients is not critical, although it is convenient first to prepare an oil concentrate containing from about 50% to about 95% by weight of the oil-soluble ingredients and from about 5% to about 50% by weight of the oil and then to emulsify the concentrate with water or a water solution containing any desired water-soluble additives in appropriate proportions.

Aqueous Compositions

The invention includes aqueous compositions which are characterized by an aqueous phase. These aqueous compositions include solutions, micelle dispersions, micro emulsions, and the like. Preferably, the aqueous phase is a continuous aqueous phase. These aqueous compositions usually contain at least about 40% by weight water. Such aqueous compositions encompass both concentrates containing from about 40% to about 70% by weight, preferably from about 40% to about 65% by weight water, and water-based functional fluids containing at least about 40% by weight and generally at least about 70% by weight of water, and an effective amount of the antioxidant compositions of the invention to improve the antioxidant characteristics of said aqueous compositions. Preferably, the antioxidant composition of the invention are present in these aqueous compositions at levels in the range of from about 0.01% to about 15%, more preferably from about 0.1% to about 10% by weight, more preferably from about 0.1% to about 5% by weight of said aqueous compositions. The concentrates generally contain less than about 50% by weight, preferably less than about 25% by weight, more preferably less than about 15% by weight, and still more preferably less than about 6% by weight hydrocarbon oil. The water-based functional fluids preferably contain less than about 15% by weight, more preferably less than about 5% by weight, and more preferably less than about 2% by weight hydrocarbon oil.

These concentrates and water-based functional fluids can optionally include other conventional additives commonly employed in water-based functional fluids. These conventional additives include dispersants, solubilizers, surfactants, functional additives, corrosion-inhibitors, shear stabilizing agents, bactericides, dyes, water-softeners, odor masking agents, anti-foam agents, and the like.

The concentrates are analogous to the water-based functional fluids except that they contain less water and proportionately more of the other ingredients. The concentrates can be converted to water-based functional fluids by dilution with water. This dilution is usually done by standard mixing techniques. This is often a convenient procedure since the concentrate can be shipped to the point of use before additional water is added. Thus, the cost of shipping a substantial amount of the water in the final water-based functional fluid is saved. Only the water necessary to formulate the concentrate (which is determined primarily by ease of handling and convenience factors), need be shipped.

Generally these water-based functional fluids are made by diluting the concentrates with water, wherein the ratio of water to concentrate is usually in the range of about 80:20 to about 99:1 by weight. As can be seen when dilution is carried out within these ranges, the final water-based functional fluid contains, at most, an insignificant amount of hydrocarbyl oil.

Also included within the invention are methods for preparing aqueous compositions, including both concentrates and water-based functional fluids, containing other conventional additives commonly employed in water-based functional fluids. These methods comprise the steps of:

(1) mixing the composition of the invention with such other conventional additives either simultaneously or sequentially to form a dispersion or solution; optionally (2) combining said dispersion or solution with water to form said aqueous concentrate; and/or (3) diluting said dispersion or solution, or concentrate with water wherein the total amount of water used is in the amount required to provide the desired concentration of the composition of the invention and other functional additives in said concentrates or said water-based functional fluids.

These mixing steps are carried out using conventional equipment and generally at room or slightly elevated temperatures, usually below 100° C. and often below 50° C. As noted above, the concentrate can be formed and then shipped to the point of use where it is diluted with water to form the desired water-based functional fluid. In other instances the finished water-based functional fluid can be formed directly in the same equipment used to form the concentrate or the dispersion or solution.

Dispersants and/or solubilizers that are useful in preparing the aqueous compositions of the present invention include the nitrogen-containing, phosphorus-free carboxylic solubilizers disclosed in U.S. Pat. Nos. 4,329,249; 4,368,133; 4,435,297; 4,447,348; and 4,448,703. These patents are incorporated herein by reference. Briefly, these dispersants and/or solubilizers are made by reacting (I) at least one carboxylic acid acylating agent having at least one hydrocarbyl-based substituent of at least about 12 to about 500 carbon atoms with (II) at least one (a) N-(hydroxyl-substituted hydrocarbyl) amine, (b) hydroxyl-substituted poly(hydrocarbyloxy) analog of said amine (a), or (c) mixtures of (a) and (b). Preferred acylating agents include the substituted succinic acids or anhydrides. Preferred amines include the primary, secondary and tertiary alkanol amines or mixtures thereof. These dispersant/solubilizers are preferably used at effective levels to disperse or dissolve the various additives, particularly the functional additives discussed below, in the concentrates and/or water-based functional fluids of the present invention. In a particularly preferred embodiment of the present invention, the dispersant/solubilizer is the reaction product of a polyisobutenyl-substituted succinic anhydride with diethylethanolamine or a mixture of diethylethanolamine and ethanolamine.

The surfactants that are useful can be of the cationic, anionic, nonionic or amphoteric type. Many such surfactants of each type are known to the art. See, for example, McCutcheon's "Emulsifiers & Detergents", 1981, North American Edition, published by McCutcheon Division, MC Publishing Co., Glen Rock, N.J., U.S.A., which is hereby incorporated by reference for its disclosures in this regard.

Among the nonionic surfactant types are the alkylene oxide-treated products, such as ethylene oxide-treated phenols, alcohols, esters, amines and amides. Ethylene oxide/propylene oxide block copolymers are also useful nonionic surfactants. Glycerol esters and sugar esters are also known to be nonionic surfactants. A typical nonionic surfactant class useful with the present invention are the alkylene oxide-treated alkyl phenols such as the ethylene oxide alkyl phenol condensates sold by the Rohm & Haas Company. A specific example of these is Triton X-100 which contains an average of 9–10 ethylene oxide units per molecule, has an HLB value of about 13.5 and a molecular weight of about 628. Many other suitable nonionic surfactants are known; see, for example, the aforementioned McCutcheon's as well as the treatise "Non-Ionic Surfactants" edited by Martin J. Schick, M. Dekker Co., New York, 1967, which is herein incorporated by reference for its disclosures in this regard.

As noted above, cationic, anionic and amphoteric surfactants can also be used. Generally, these are all hydrophilic surfactants. Anionic surfactants contain negatively charged polar groups while cationic surfactants contain positively charged polar groups. Amphoteric dispersants contain both types of polar groups in the same molecule. A general survey of useful surfactants is found in Kirk-Othmer Encyclopedia of Chemical Technology, Second Edition, Volume 19, page 507 et seq. (1969, John Wiley and Son, New York) and the aforementioned compilation published under the name of McCutcheon's. These references are both hereby incorporated by reference for their disclosures relating to cationic, amphoteric and anionic surfactants.

Among the useful anionic surfactant types are the widely known carboxylate soaps, organo sulfates, sulfonates, sulfocarboxylic acids and their salts, and phosphates. Useful cationic surfactants include nitrogen compounds such as amine oxides and the wellknown quaternary ammonium salts. Amphoteric surfactants include amino acid-type materials and similar types. Various cationic, anionic and amphoteric dispersants are available from the industry, particularly from such companies as Rohm & Haas and Union Carbide Corporation, both of America. Further information about anionic and cationic surfactants also can be found in the texts "Anionic Surfactants", Parts II and III, edited by W. M. Linfield, published by Marcel Dekker, Inc., New York, 1976 and "Cationic Surfactants", edited by E. Jungermann, Marcel Dekker, Inc., New York, 1976. Both of these references are incorporated by reference for their disclosures in this regard.

These surfactants, when used, are generally employed in effective amounts to aid in the dispersal of the various additives, particularly the functional additives discussed below, in such systems.

The functional additives that can be used are typically oil-soluble, water-insoluble additives which function in conventional oil-based systems as extreme pressure agents, anti-wear agents, load-carrying agents, friction modifiers, lubricity agents, etc. They can also function as anti-slip agents, film formers and friction modifiers. As is well known, such additives can function in two or more of the above-mentioned ways; for example, extreme pressure agents often function as load-carrying agents.

The term "oil-soluble, water-insoluble functional additive" refers to a functional additive which is not soluble in water above a level of about 1 gram per 100 milliliters of water at 25° C., but is soluble in mineral oil to the extent of at least 1 gram per liter at 25° C.

These functional additives can also include certain solid lubricants such as graphite, molybdenum disulfide and polytetrafluoroethylene and related solid polymers.

These functional additives can also include frictional polymer formers. Briefly, these are potential polymer forming materials which are dispersed in a liquid carrier at low concentration and which polymerize at rubbing or contacting surfaces to form protective polymeric films on the surfaces. The polymerizations are believed to result from the heat generated by the rubbing and, possibly, from catalytic and/or chemical action of the freshly exposed surface. A specific example of such materials is dilinoleic acid and ethylene glycol combinations which can form a polyester frictional polymer film. These materials are known to the art and descriptions of them are found, for example, in the journal "Wear", Volume 26, pages 369-392, and West German Published Patent Application 2,339,065. These disclosures are hereby incorporated by reference for their discussions of frictional polymer formers.

Typically these functional additives are known metal or amine salts of organo sulfur, phosphorus, boron or carboxylic acids which are the same as or of the same type as used in oil-based fluids. Typically such salts are of carboxylic acids of 1 to 22 carbon atoms including both aromatic and aliphatic acids; sulfur acids such as alkyl and aromatic sulfonic acids and the like; phosphorus acids such as phosphoric acid, phosphorus acid, phosphinic acid, acid phosphate esters and analogous sulfur homologs such as the thiophosphoric and dithiophosphoric acids and related acid esters; boron acids include boric acid, acid borates and the like. Useful functional additives also include metal dithiocarbamates such as molybdenum and antimony dithiocarbamates; as well as dibutyl tin sulfide, tributyl tin oxide, phosphates and phosphites; borate amine salts, chlorinated waxes; trialkyl tin oxide, molybdenum phosphates, and chlorinated waxes.

Mainly such functional additives are known to the art. For example, descriptions of additives useful in conventional oil-based systems and in the aqueous systems of this invention are found in "Advances in Petroleum Chemistry and Refining", Volume 8, edited by John J. McKetta, Interscience Publishers, New York, 1963, pages 31-38 inclusive; Kirk-Othmer "Encyclopedia of Chemical Technology", Volume 12, Second Edition, Interscience Publishers, New York, 1967, page 575 et seq.; "Lubricant Additives" by M. W. Ranney, Noyes Data Corporation, Park Ridge, N.J., U.S.A., 1973; and "Lubricant Additives" by C. V. Smalheer and R. K. Smith, The Lezius-Hiles Co., Cleveland, Ohio, U.S.A. These references are hereby incorporated by reference for their disclosures of functional additives useful in the systems of this invention.

In certain of the typical aqueous systems of the invention, the functional additive is a sulfur or chloro-sulfur extreme pressure agent, known to be useful in oil-base systems. Such materials include chlorinated aliphatic hydrocarbons, such as chlorinated wax; organic sulfides and polysulfides, such as benzyl-disulfide, bis-(chlorobenzyl)disulfide, dibutyl tetrasulfide, sulfurized sperm oil, sulfurized methyl ester of oleic acid, sulfurized alkylphenol, sulfurized dipentene, sulfurized terpene, and sulfurized Diels-Alder adducts; phosphosulfurized hydrocarbons, such as the reaction product of phosphorus sulfide with turpentine or methyl oleate; phosphorus esters such as the dihydrocarbyl and trihydrocarbyl phosphites, i.e., dibutyl phosphite, diheptyl phosphite, dicyclohexyl phosphite, pentylphenyl phosphite, dipentylphenyl phosphite, tridecyl phosphite, distearyl phosphite and polypropylene substituted phenol phosphite; metal thiocarbamates, such as zinc dioctyldithiocarbamate and barium heptylphenol dithiocarbamate; and Group II metal salts of phosphorodithioic acid, such as zinc dicyclohexyl phosphorodithioate, and the zinc salts of a phosphorodithioic acid.

The functional additive can also be a film former such as a synthetic or natural latex or emulsion thereof in water. Such latexes include natural rubber latexes and polystyrene butadienes synthetic latex.

The functional additive can also be an anti-chatter or anti-squawk agent. Examples of the former are the amide metal dithiophosphate combinations such as disclosed in West German Patent No. 1,109,302; amine salt-azomethine combinations such as disclosed in British Patent Specification No. 893,977; or amine dithiophosphate such as disclosed in U.S. Pat. No. 3,002,014. Examples of anti-squawk agents are N-acyl-sarcosines and derivatives thereof such as disclosed in U.S. Pat. Nos. 3,156,652 and 3,156,653; sulfurized fatty acids and esters thereof such as disclosed in U.S. Pat. Nos. 2,913,415 and 2,982,734; and esters of dimerized fatty acids such as disclosed in U.S. Pat. No. 3,039,967. The above-cited patents are incorporated herein by reference for their disclosure as pertinent to anti-chatter and anti-squawk agents useful as a functional additive in the aqueous systems of the present invention.

Specific examples of functional additives useful in the aqueous compositions of this invention include the following commercially available products.

TABLE II

| Functional Additive Tradename | Chemical Description | Supplier |
|---|---|---|
| Anglamol 32 | Chlorosulfurized hydrocarbon | Lubrizol[1] |
| Anglamol 75 | Zinc dialkyl phosphate | Lubrizol[1] |
| Molyvan L | A thiaphosphomolybdate | Vanderbilt[2] |
| Lubrizol-5315 | Sulfurized cyclic carboxylate ester | Lubrizol[1] |

TABLE II-continued

| Functional Additive Tradename | Chemical Description | Supplier |
| --- | --- | --- |
| Emcol TS 230 | Acid phosphate ester | Witco[3] |

[1]The Lubrizol Corporation, Wickliffe, Ohio, U.S.A.
[2]R.T. Vanderbilt Company, Inc., New York, N.Y., U.S.A.
[3]Witco Chemical Corp., Organics Division, Houston, Texas, U.S.A.

Mixtures of two or more of any of the aforedescribed functional additives can also be used.

Typically, a functionally effective amount of the functional additive is present in the aqueous systems of this invention. For example, if the functional additive is intended to serve primarily as a load-carrying agent, it is present in a load-carrying amount.

The aqueous compositions of this invention often contain at least one inhibitor for corrosion of metals. These inhibitors can prevent corrosion of either ferrous or non-ferrous metals (e.g., copper, bronze, brass, titanium, aluminum and the like) or both. The inhibitor can be organic or inorganic in nature. Usually it is sufficiently soluble in water to provide a satisfactory inhibiting action though it can function as a corrosion-inhibitor without dissolving in water, it need not be water-soluble. Many suitable inorganic inhibitors useful in the aqueous systems of the present invention are known to those skilled in the art. Included are those described in "Protective Coatings for Metals" by Burns and Bradley, Reinhold Publishing Corporation, Second Edition, Chapter 13, pages 596-605. This disclosure relative to inhibitors is hereby incorporated by reference. Specific examples of useful inorganic inhibitors include alkali metal nitrites, sodium di- and tripolyphosphate, potassium and dipotassium phosphate, alkali metal borate and mixtures of the same. Many suitable organic inhibitors are known to those of skill in the art. Specific examples include hydrocarbyl amine and hydroxy-substituted hydrocarbyl amine neutralized acid compound, such as neutralized phosphates and hydrocarbyl phosphate esters, neutralized fatty acids (e.g., those having about 8 to about 22 carbon atoms), neutralized aromatic carboxylic acids (e.g., 4-tert-butyl benzoic acid), neutralized naphthenic acids and neutralized hydrocarbyl sulfonates. Mixed salt esters of alkylated succinimides are also useful. Particularly useful amines include the alkanol amines such as ethanol amine, diethanol amine. Mixtures of two or more of any of the afore-described corrosion inhibitors can also be used. The corrosion inhibitor is usually present in concentrations in which they are effective in inhibiting corrosion of metals with which the aqueous composition comes in contact.

The aqueous compositions of the present invention (particularly those that are used in cutting or shaping of metal) can also contain at least one polyol with inverse solubility in water. Such polyols are those that become less soluble as the temperature of the water increases. They thus can function as surface lubricity agents during cutting or working operations since, as the liquid is heated as a result of friction between a metal workpiece and worktool, the polyol of inverse solubility "plates out" on the surface of the workpiece, thus improving its lubricity characteristics.

The aqueous compositions of the present invention can also include at least one bactericide. Such bactericides are well known to those of skill in the art and specific examples can be found in the aforementioned McCutcheon publication "Functional Materials" under the heading "Antimicrobials" on pages 9-20 thereof. This disclosure is hereby incorporated by reference as it relates to suitable bactericides for use in the aqueous compositions or systems of this invention. Generally, these bactericides are water-soluble, at least to the extent to allow them to function as bactericides.

The aqueous compositions of the present invention can also include such other materials as dyes, e.g., an acid green dye; water softeners, e.g., ethylene diamine tetraacetate sodium salt or nitrilo triacetic acid; odor masking agents, e.g., citronella, oil of lemon, and the like; and anti-foamants, such as the well-known silicone anti-foamant agents.

The aqueous compositions of this invention may also include an anti-freeze additive where it is desired to use the composition at a low temperature. Materials such as ethylene glycol and analogous polyoxyalkylene polyols can be used as anti-freeze agents. Clearly, the amount use will depend on the degree of anti-freeze protection desired and will be known to those of ordinary skill in the art.

It should also be noted that many of the ingredients described above for use in making the aqueous compositions of this invention are industrial products which exhibit or confer more than one property on such aqueous systems. Thus, a single ingredient can provide several functions thereby eliminating or reducing the need for some other additional ingredient. Thus, for example, an extreme pressure agent such as tributyl tin oxide can also function as a bactericide.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A composition comprising
(A) a compound represented by the formula

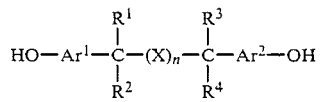

wherein $Ar^1$ and $Ar^2$ are independently mononuclear or polynuclear, substituted or unsubstituted aromatic groups; $R^1$, $R^2$, $R^3$ and $R^4$ are independently hydrogen or hydrocarbyl groups of from 1 to about 25 carbon atoms; X is at least one divalent sulfur atom, sulfone group, sulfoxide group, or a mixture thereof; and n is a number ranging from 1 to about 5; and (B) a compound represented by the formula

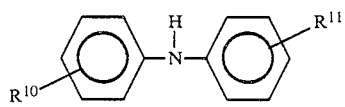

wherein $R^{10}$ and $R^{11}$ are independently hydrogen or an alkylated group containing from 4 to 20 carbon atoms wherein the weight ratio of (B) to (A) is about 0.01 to about 100 parts of (B) per parts of (A).

2. The composition of claim 1 wherein component (A) comprises at least one compound represented by the formula

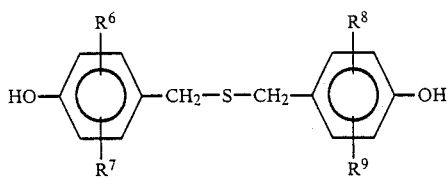

wherein $R^6$, $R^7$, $R^8$ and $R^9$ are independently hydrogen, halogen, OH, $NH_2$, SH, $NO_2$ or hydrocarbyl groups from 1 to about 50 carbon atoms.

3. The composition of claim 1 wherein component (A) comprises at least one compound represented by the formula

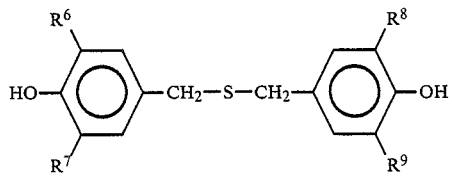

wherein $R^6$, $R^7$, $R^8$ and $R^9$ are independently hydrogen, halogen, OH, $NH_2$, SH, $NO_2$ or hydrocarbyl groups of from 1 to about 16 carbon atoms.

4. The composition of claim 3 wherein $R^6$, $R^7$, $R^8$ and $R^9$ are each tertiary butyl groups.

5. The composition of claim 1 wherein component (B) comprises a nonylateddiphenylamine.

6. The composition of claim 1 wherein component (A) is formed by reacting at least one hydroxyaromatic compound with at least one aldehyde and/or ketone, and at least one sulfide, in the presence of a solvent.

7. The composition of claim 1 wherein component (A) is formed by reacting at least one hydroxyaromatic compound with at least one aldehyde and/or ketone in the presence of a first solvent to form an intermediate product, then reacting said intermediate product with at least one sulfide in the presence of a second solvent to form said component (A).

8. The composition of claim 6 wherein said solvent is methanol.

9. The composition of claim 6 wherein said hydroxyaromatic compound comprises 2,6-di-tert-butylphenol.

10. The composition of claim 6 wherein said sulfide is an alkali metal sulfide.

11. The composition of claim 6 wherein said sulfide is sodium sulfide.

12. The composition of claim 6 wherein said aldehyde is formaldehyde.

13. The composition of claim 7 wherein said first solvent and said second solvent each comprise methanol.

14. The composition of claim 7 wherein said hydroxyaromatic compound comprises 2,6-di-tert-butylphenol.

15. The composition of claim 7 wherein said sulfide is an alkali metal sulfide.

16. The composition of claim 7 wherein said sulfide is sodium sulfide.

17. The composition of claim 7 wherein said aldehyde is formaldehyde.

18. A composition comprising:
(A) a compound represented by the formula

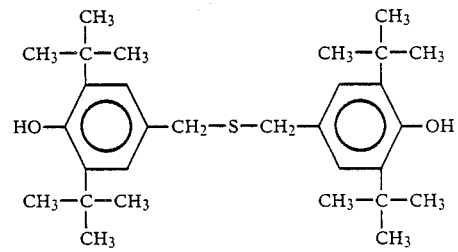

and;
(B)

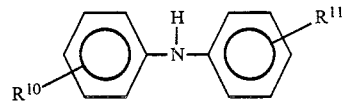

wherein $R^{10}$ and $R^{11}$ are independently hydrogen or an alkylated group containing from 4 to 20 carbon atoms wherein the weight ratio of (B) to (A) is from about 0.01 to about 100 parts of (B) per parts of (A).

19. A concentrate comprising from about 0.2% to 90% by weight of the composition of claim 1 and a diluent.

20. A lubricant or functional fluid comprising a major amount of an oil, and, an effective amount of the composition of claim 1 to improve the antioxidant characteristics of said lubricant or functional fluid.

21. An aqueous composition comprising a major amount of water, and an effective amount of the composition of claim 1 to improve the antioxidant characteristics of said aqueous composition.

22. An emulsion comprising an organic phase, an aqueous phase, and an effective amount of the composition of claim 1 to improve the antioxidant characteristics of said emulsion.

23. A rust- and oxidation-inhibited oil, turbine oil and/or compressor oil comprising: a base oil;
from about 0.01% to about 0.25% by weight of a compound represented by the formula

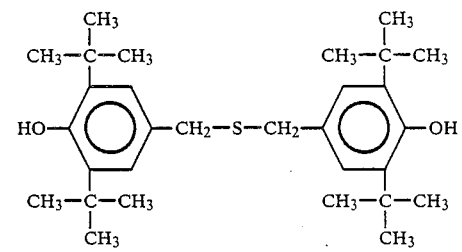

from about 0.01 to about 0.5% by weight of a compound represented by the formula

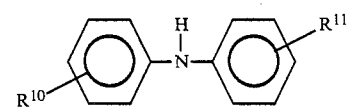

wherein $R^{10}$ and $R^{11}$ are independently hydrogen or an alkylated group containing from 4 to 20 carbon atoms;

from about 0.01 to about 0.1% by weight of a diluent oil;

from about 0.01 to about 0.1% by weight of at least one rust-inhibitor;

from about 0.01 to about 0.1% by weight of at least one metal deactivator;

from about 0.001 to about 0.1% by weight of at least one demulsifier; and from about 0.1 to about 0.5% by weight of at least one auxiliary antioxidant.

24. A hydraulic oil and/or compressor oil comprising: a base oil;

from about 0.01% to about 0.25% by weight of a compound represented by the formula

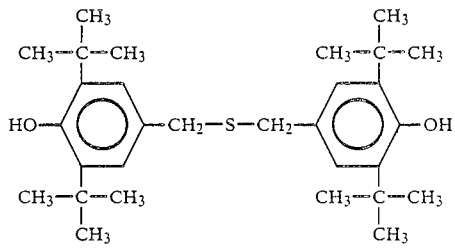

from about 0.01 to about 0.5% by weight of a compound represented by the formula

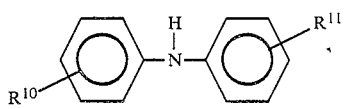

wherein $R^{10}$ and $R^{11}$ are independently hydrogen or an alkylated group containing from 4 to 20 carbon atoms;
from about 0.01 to about 0.1% by weight of a diluent oil;
from about 0.1 to about 1% by weight of at least one anit-wear agent;
from about 0.01 to about 0.1% by weight of at least one rust-inhibitor;
from about 0.01 to about 0.1% by weight of at least one metal deactivator; and
from about 0.001 to about 0.1% by weight of at least one demulsifier.

* * * * *

UNITED STATES PATENT AND TRADEMARK OFFICE
CERTIFICATE OF CORRECTION

PATENT NO. : 4,846,985

DATED : July 11, 1989

INVENTOR(S) : S. Q. Abbas Rizvi et al

It is certified that error appears in the above—identified patent and that said Letters Patent is hereby corrected as shown below:

Column 1, line 14, "Prominant" should be --Prominent--.

Column 2, lines 49-64,

"Sulfoxide gripus (e.g.,

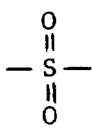

hydrocarbyl).
hydrocrbyl).
Sulfone groups (e.g.,

hydrocarbyl);"

should be

--Sulfone groups (e.g., $-\overset{O}{\underset{O}{\overset{\|}{\underset{\|}{S}}}}-$ hydrocarbyl);

Sulfoxide groups (e.g., $-\overset{O}{\overset{\|}{S}}-$ hydrocarbyl).--

Column 12, line 40, "mangnesium" should be --magnesium--.

Column 19, line 4, "mono-(3,5dioctylphe-" should be
    --mono-(3,5-dioctylphe- --.

UNITED STATES PATENT AND TRADEMARK OFFICE
CERTIFICATE OF CORRECTION

PATENT NO. : 4,846,985

DATED : July 11, 1989

INVENTOR(S) : S. Q. Abbas Rizvi et al

It is certified that error appears in the above—identified patent and that said Letters Patent is hereby corrected as shown below:

Column 20, line 34, "aving" should be --having--.

Column 20, line 38, "talc" should be --tall--.

Signed and Sealed this

Twenty-fourth Day of July, 1990

Attest:

HARRY F. MANBECK, JR.

*Attesting Officer*    *Commissioner of Patents and Trademarks*